(12) United States Patent
Hoegerle et al.

(10) Patent No.: US 12,220,287 B2
(45) Date of Patent: Feb. 11, 2025

(54) SURGICAL DEVICE WITH INTEGRATED RFID READOUT ANTENNA

(71) Applicant: Aesculap AG, Tuttlingen (DE)

(72) Inventors: Roland-Alois Hoegerle, Tuttlingen (DE); Frederick Lenzenhuber, Tuttlingen (DE); Ralf Pfister, Trossingen (DE); André Buerk, Villingen-Schwenningen (DE); Martin Machill, Rietheim-Weilheim (DE)

(73) Assignee: Aesculap AG, Tuttlingen (DE)

( * ) Notice: Subject to any disclaimer, the term of this patent is extended or adjusted under 35 U.S.C. 154(b) by 58 days.

(21) Appl. No.: 17/767,651

(22) PCT Filed: Oct. 9, 2020

(86) PCT No.: PCT/EP2020/078410
§ 371 (c)(1),
(2) Date: Apr. 8, 2022

(87) PCT Pub. No.: WO2021/069662
PCT Pub. Date: Apr. 15, 2021

(65) Prior Publication Data
US 2024/0081945 A1 Mar. 14, 2024

(30) Foreign Application Priority Data
Oct. 11, 2019 (DE) .................... 10 2019 127 468.0

(51) Int. Cl.
*A61B 90/98* (2016.01)
*A61B 17/00* (2006.01)
*A61B 90/00* (2016.01)
*H01R 13/03* (2006.01)
*H01R 13/66* (2006.01)

(52) U.S. Cl.
CPC .............. *A61B 90/98* (2016.02); *A61B 17/00* (2013.01); *A61B 90/08* (2016.02); *H01R 13/03* (2013.01);
(Continued)

(58) Field of Classification Search
CPC .......... A61B 90/98; A61B 2017/00221; A61B 2017/00398; A61B 2017/00477; A61B 2090/0803; A61B 2090/0804
See application file for complete search history.

(56) References Cited

U.S. PATENT DOCUMENTS 8,157,826 B2   4/2012 Deng et al.
9,084,586 B2   7/2015 Hafner et al.
(Continued)

FOREIGN PATENT DOCUMENTS

DE   102008024438 A1   11/2009
DE   102011050192 A1   11/2012

OTHER PUBLICATIONS

Search Report received in German Application No. 10 2019 127 468.0 dated Jul. 1, 2020, with translation, 17 pages.
(Continued)

*Primary Examiner* — Nabil H Syed
*Assistant Examiner* — Cal J Eustaquio
(74) *Attorney, Agent, or Firm* — CM Law; Christopher A. Rothe

(57) ABSTRACT

A surgical device includes a surgical application part having an electric motor with motor windings and an electrical supply cable having a plurality of lines. The electrical supply cable can be connected to the surgical application part at a first end and to a control unit for controlling the electric motor at a second end. The surgical device includes at least one readout antenna which is integrated/provided in the surgical application part or the electrical supply cable. The at least one readout antenna can be supplied with voltage and, as an additional element separate from the motor windings, can activate and read out an RFID chip that is/can be arranged near to the at least one readout antenna, in order
(Continued)

to transmit data bidirectionally between the RFID chip and the control unit via the electrical supply cable.

12 Claims, 9 Drawing Sheets

(52) U.S. Cl.
CPC .... *H01R 13/66* (2013.01); *A61B 2017/00221* (2013.01); *A61B 2017/00398* (2013.01); *A61B 2017/00477* (2013.01); *A61B 2090/0803* (2016.02); *A61B 2090/0804* (2016.02)

(56) References Cited

U.S. PATENT DOCUMENTS

| 9,101,337 | B2 | 8/2015 | Hoegerle et al. | |
|---|---|---|---|---|
| 2002/0130783 | A1* | 9/2002 | Hogan | F04D 15/0088 |
| | | | | 340/853.1 |
| 2007/0083111 | A1* | 4/2007 | Hossack | A61B 8/12 |
| | | | | 600/407 |
| 2008/0262654 | A1 | 10/2008 | Omori et al. | |
| 2011/0208170 | A1 | 8/2011 | Hafner et al. | |
| 2015/0272654 | A1 | 10/2015 | Esch et al. | |
| 2016/0239001 | A1* | 8/2016 | Chin | G07C 9/00 |
| 2018/0256287 | A1 | 9/2018 | Bosisio et al. | |

OTHER PUBLICATIONS

Search Report received in International Application No. PCT/EP2020/078410 dated Jan. 21, 2021, with translation, 6 pages.
Written Opinion received in International Application No. PCT/EP2020/078410 dated Jan. 21, 2021, with translation, 13 pages.

* cited by examiner

SURGICAL DEVICE WITH INTEGRATED RFID READOUT ANTENNA

CROSS-REFERENCES TO RELATED APPLICATIONS

This application is the United States national phase entry of International Application No. PCT/EP2020/078410, filed Oct. 9, 2020, and claims priority to German Application No. 10 2019 127 468.0, filed Oct. 11, 2019. The contents of International Application No. PCT/EP2020/078410 and German Application No. 10 2019 127 468.0 are incorporated by reference herein in their entireties.

FIELD

The present invention relates to a surgical device comprising: a surgical application part having an electric motor, and an electrical supply cable having a plurality of lines, in particular three or four lines, wherein the electrical supply cable is connectable at a first end to the surgical application part and at a second end to a control unit for controlling the electric motor.

BACKGROUND

Such a surgical device is already known from DE 10 2011 050 192 A1. DE 10 2011 050 192 A1 basically discloses a surgical coupling system with two coupling devices, each of which has electrical coupling contacts that can be mechanically engaged with each other. A first coupling device is a surgical application part and a second coupling device is an electrical supply cable. The surgical application part has four pin-shaped application-part plug contacts/coupling contacts and the electrical supply cable has four socket-shaped supply-cable plug contacts/coupling contacts. The application-part plug contacts are engageable with the supply-cable plug contacts in order to mechanically couple the surgical application part to the electrical supply cable. When the surgical application part and the electrical supply cable are coupled together, at least two electrical switching positions, namely an OFF position and an ON position, are adjustable. In the OFF position, an encoding/detection resistor can be used to determine which type of electric motor is installed in the surgical application part. From this information, a control unit can generally determine the connected surgical application part. In the ON position, the switching circuit in which the encoding/detection resistor is located is short-circuited (deactivated) and the surgical device is ready for a surgical procedure (motor operation).

It is known that such surgical devices are not disposable products and therefore have to be processed after use, for example after a surgical procedure. A typical processing cycle includes, for example, cleaning in a washer-disinfector (WD), oiling if necessary as well as sterilization. Frequent processing/reprocessing leads to quality losses in medical products, to which the surgical device of the present invention belongs.

Against this background, the prior art, in particular DE 10 2011 050 192 A1, has the basic disadvantage that the number of processing cycles through which the surgical device has passed is not counted and thus information about the number of processing cycles is not recorded and documented. Information about the number of processing cycles the surgical device has undergone could be used, for example, to make statements about the general condition of the surgical device, its service life, a maintenance interval, suitability for a follow-up operation, damage to the surgical device, etc.

A user cannot tell from the product/surgical device/part thereof how often processing/reprocessing has been carried out. This also has the consequence that the products/devices have to be subjected to a defined maintenance interval, e.g. a specific time, even if maintenance is not actually required. The fact that the number of processing cycles is not counted is also disadvantageous in terms of providing evidence in the event of complaints, tracking and lifecycle management.

SUMMARY

Against this background, it is the object of the present invention to avoid or at least reduce these disadvantages of the prior art. In particular, the present invention is based on the object that the processing cycles, which the surgical device or a part/component thereof has undergone, are to be counted, recorded and documented in order to be able to further process the knowledge gained from this information.

Advantageous embodiments and further developments of the invention are explained below.

The invention relates firstly to a surgical device comprising: a surgical application part with an electric motor having motor windings, and a cable/electrical supply cable having a plurality of, in particular three or four, lines, wherein the electrical supply cable is connectable at a first end to the surgical application part and at a second end to a control unit for controlling the electric motor. The surgical device comprises at least one readout antenna which is integrated/provided in the surgical application part or the electrical supply cable, is capable of being supplied with voltage, is designed as an additional element separate from the motor windings and is adapted to excite and read out an RFID chip arranged or arrangeable near the readout antenna, in particular in the close proximity, in order to be able to transmit data bidirectionally between the RFID chip and the control unit via the electrical supply cable.

The core of the invention is to integrate a readout antenna in the surgical application part or in the electrical supply cable (in particular as an additional element separate from the motor windings in an electrical switching circuit of the surgical application part or in an electrical switching circuit of the electrical supply cable), and to provide/install, in the surgical device (for example in the surgical application part or in the electrical supply cable or in another provided component such as a tool attachment), an RFID chip, which is arranged very close to/adjacent to/abutting/bordering the readout antenna. If the readout antenna is integrated in an electrical switching circuit of the surgical application part or of the electrical supply cable, it can be supplied with voltage and can excite and read out the RFID chip.

Energy and information/data can preferably be transmitted bidirectionally between the RFID chip and a control unit connected to the electrical supply cable via the readout antenna integrated in the surgical application part or the electrical supply cable. The control unit can therefore determine how often the surgical device has already been used and can also write the repeated use of the surgical device or a part of the surgical device on the RFID chip. This means that the RFID chip always contains the number of operations/surgical procedures and therefore also the number of processing cycles.

According to the invention, data on the number of processing cycles in the surgical device and in particular in a part/component of the surgical device (surgical application part, electrical supply cable or another component/accessory such as a tool attachment) is stored. This means that parts/components of the same type can be distinguished. For example, information about the number of processing cycles is stored in a large number of surgical application parts, so that a processing history is accessible for each surgical application part and information about the general condition, service life, required maintenance, etc. can be obtained from this.

If required, the RFID chip can also be read out with an external reader with its own readout antenna in order to retrieve a processing history when the surgical device/part/component thereof is not in use (for example during handling, preparation for use). The geometrical installation situation of the RFID chip, the surrounding components and the shape of the readout antenna have to be chosen appropriately in order to ensure that reliable reception (signal amplification) or, in general, reliability of data transmission can be realized both between the readout antenna and the RFID chip and between the external reader and the RFID chip. In particular, the readout antenna may be integrated into the surgical application part outside the electric motor or into the electric supply cable. In particular, it has to be ensured that a distance between readout antenna and RFID chip as well as a distance between external reader and RFID chip is not too large. This can be realized, for example, if the RFID chip is installed near an outer surface of a component of the surgical device and the readout antenna is arranged in the component near the RFID chip. This ensures very good reception of the RFID chip/RFID tag in the product/surgical device.

In particular, the number of processing cycles stored in the product/part itself can be used to infer a general condition of the product (runtime determination), a service life or end of service life, a maintenance interval, power/performance, suitability for a subsequent operation and product damage due to lack of care or temperature overshoots/undershoots. Since the RFID chip carries the information or information are being/are documented in the product, transparency can be realized in the event of service.

With the present invention, customized services and individually tailored business models (e.g. pay per use, etc.) can be offered to a user or customer.

Surgical application parts are understood to be, for example, handpieces, shaver handpieces, pistol handpieces, etc.

In principle, two, three, four or more integrated/provided readout antennas that can be supplied with voltage can also be provided in the surgical application part or the electrical supply cable.

Preferably, in addition to the surgical application part and the electrical supply cable, the surgical device comprises the control unit for controlling the electric motor.

Furthermore, the readout antenna is preferably provided/integrated in the surgical application part and, in addition to the readout antenna, a detection resistor is provided in the surgical application part, which serves to detect the surgical application part, in particular the electric motor thereof, by the control unit. In other words, the readout antenna can be installed instead of or together with a detection resistor in the surgical application part (a switching circuit/current circuit thereof). Accordingly, backward compatibility with existing products is possible in principle. However, it should be noted that using the readout antenna in combination with the RFID chip, far more information can be obtained about the surgical application part than via the detection resistor, so that the detection resistor can in principle also be dispensed with.

It is advantageous if the readout antenna and the RFID chip are arranged or arrangeable at a distance from each other of less than or equal to 1 cm, preferably less than or equal to 5 mm, particularly preferably less than or equal to 2 mm. If such a distance between the readout antenna and the RFID chip is realized, it can be assumed that the readout antenna is located close to the RFID chip (in close proximity). It can therefore be ensured that excitation/readout of the RFID chip by the readout antenna and bidirectional data transmission between the RFID chip and the control unit are possible.

It is advantageous if the readout antenna is meander-shaped or spiral-shaped or coil-shaped or helix-shaped.

According to a preferred embodiment, an antenna carrier may be incorporated in the surgical application part or in the electrical supply cable, for example, which carries a readout antenna in the form of a coil/which is coil-shaped.

According to a further preferred embodiment, for example, the surgical application part or the electrical supply cable can incorporate an insertion part, in particular an insertion plate, which is designed as a plane circuit board or a flexible circuit board, on which a meander-shaped readout antenna is applied.

According to a further preferred embodiment, for example, an insertion part or a functional part made of plastic may be incorporated in the surgical application part or in the electrical supply cable, and a meander-shaped readout antenna may be printed or vapor-deposited onto the insertion part/functional part made of plastic. In particular, the insertion part/functional part may be a sleeve made of plastic, which forms an insulating contact carrier.

Advantageously, the electrical supply cable has precisely/exactly three lines, in particular litz wires.

If only three lines/litz wires are provided in the electrical supply cable, a small diameter of the electrical supply cable can be realized. An important aspect of the present invention is that all intended functions of the surgical device (recognition of the surgical application part, bidirectional data transmission/read-write and motor operation) are implemented with an electrical supply cable having only three lines. Preferably, the number of lines in the electrical supply cable corresponds to the number of motor connections/motor windings. The further functions (besides the motor operation) are preferably to be realized by intelligent circuit technology, and thus without having to increase the thickness of the electrical supply cable. Accordingly, one or more readout antennas are preferably integrated in the surgical application part or in the electrical supply cable in such a way that all intended functions (recognition of surgical application part/accessories, data transmission read/write and motor operation) are only possible via three lines/litz wires in the electrical supply cable to the control unit. This allows the smallest possible cable diameter and thus the best possible flexibility and ergonomics of a cable-based system when working.

However, it is also conceivable in principle that the electrical supply cable has its own line for the readout antenna and thus four lines are provided, which, however, has the disadvantage of making the electrical supply cable thicker.

It is practical if the electric motor provided in the surgical application part has three motor windings, which can be supplied with current and can be driven via the three lines provided in the electric supply cable. Preferably, the three motor windings are interconnected in a star configuration.

Advantageously, the (passive) RFID chip is integrated in the surgical application part. The RFID chip preferably has a glass shell (glass tag).

It is advantageous if the surgical application part has a plurality of, in particular three or four, application-part plug contacts and the electrical supply cable has a plurality of, in particular three or four, supply-cable plug contacts, wherein the application-part plug contacts and the supply-cable plug contacts are engageable with each other in order to couple the surgical application part, in particular mechanically, to the electrical supply cable.

When the surgical application part and the electrical supply cable are coupled to each other, at least two electrical switching positions, namely an OFF position and an ON position, are advantageously adjustable, wherein in the OFF position the readout antenna is supplied with voltage and the RFID chip can thus be excited and read out, and wherein in the ON position the readout antenna is not supplied with voltage, in particular a switching circuit containing the readout antenna gets/is short-circuited and thus taken out of operation.

The readout antenna is therefore designed, for example, in the form of a coil and is installed instead of or together with an existing detection resistor in a switching circuit/current circuit in the surgical application part in such a way that the readout antenna in the OFF position is supplied with voltage via the lines/(cable) litz wires of the electrical supply cable and the RFID chip thus excited passes on its data to the control unit via the electrical supply cable. In the ON position, the switching circuit/current circuit for the readout antenna or respectively for the detection resistor is preferably short-circuited and taken out of operation.

According to a first advantageous configuration example, a first motor winding of the three motor windings is preferably connected to a first application-part plug contact in an electrically conducting manner and is connected to the readout antenna in an electrically conducting manner, and the readout antenna is in turn connected to a second application-part plug contact in an electrically conducting manner.

Preferably, according to the first configuration example, a detection resistor is additionally provided, which is connected in series to the readout antenna.

In the OFF position, the second application-part plug contact is preferably connected to the electrical supply cable in an electrically conducting manner, and the first application-part plug contact is preferably not connected to the electrical supply cable in an electrically conducting manner.

In the ON position, the first application-part plug contact is preferably connected to the electrical supply cable in an electrically conducting manner.

A second motor winding of the three motor windings is preferably connected to a third application-part plug contact in an electrically conducting manner, and a third motor winding of the three motor windings is preferably connected to a fourth application-part plug contact in an electrically conducting manner.

Advantageously, the application-part plug contacts are pin-shaped, and the supply-cable plug contacts are socket-shaped.

Preferably, first to fourth application-part plug contacts are provided, which are adapted to engage in corresponding first to fourth supply-cable plug contacts.

First and second supply-cable-plug contacts are preferably connected in an electrically conducting manner to a first line of the three lines provided in the electrical supply cable.

Preferably, the third supply-cable plug contact is connected in an electrically conducting manner to the second line of the three lines provided in the electrical supply cable.

Further preferably, the fourth supply-cable plug contact is connected in an electrically conducting manner to the third line of the three lines provided in the electrical supply cable.

Advantageously, in the OFF position the second application-part plug contact is connected to the second supply-cable plug contact in an electrically conducting manner, and the third application-part plug contact is connected to the third supply-cable plug contact in an electrically conducting manner.

It is practical if, in the OFF position, the first application-part plug contact and the first supply-cable plug contact are not connected in an electrically conducting manner, and the fourth application-part plug contact and the fourth supply-cable plug contact are not connected in an electrically conducting manner.

Preferably, all application-part plug contacts are connected to the supply-cable plug contacts in an electrically conducting manner in the ON position.

According to a second advantageous configuration example, the application-part plug contacts are pin-shaped and at least one application-part plug contact has two independent, different contact zones for different switching-circuit driving in the ON position and in the OFF position.

Preferably, the two contact zones are spaced apart in the axial direction of the pin-shaped application-part plug contact.

Further preferably, first to third application-part plug contacts are provided, which are adapted to engage in corresponding first to third supply-cable plug contacts.

Preferably, two application-part plug contacts of the three application-part plug contacts each have two independent, different contact zones for different switching-circuit driving in the ON position and the OFF position.

Preferably, the contact zones of the two application-part plug contacts are designed in such a way that when changing from the OFF position to the ON position, the contact zones do not change simultaneously but one after the other.

Advantageously, the first application-part plug contact comprises a first contact zone and a second contact zone, wherein the first contact zone is connected to the readout antenna in an electrically conducting manner, and wherein the second contact zone is connected to the first motor winding in an electrically conducting manner.

It is advantageous if the second application-part plug contact has a first contact zone and a second contact zone, wherein the first contact zone is connected to the readout antenna and the detection resistor in an electrically conducting manner, and wherein the second contact zone is connected to the second motor winding in an electrically conducting manner.

Preferably, the third application-part plug contact is connected to the third motor winding in an electrically conducting manner.

In the OFF position, the first contact zone of the first application-part plug contact is preferably connected to the first supply-cable plug contact in an electrically conducting manner, and the first contact zone of the second application-part plug contact is connected to the second supply-cable plug contact in an electrically conducting manner, and the third application-part plug contact is connected to the third supply-cable plug contact in an electrically conducting manner.

It is practical if, in the ON position, the second contact zone of the first application-part plug contact is connected to the first supply-cable plug contact in an electrically conducting manner, and the second contact zone of the second application-part plug contact is connected to the second supply-cable plug contact in an electrically conducting manner.

Preferably, the first and second contact zones are separated from each other by an insulator.

According to a third advantageous configuration example, the supply-cable plug contacts are socket-shaped and at least one supply-cable plug contact has two independent, different contact zones for different switching-circuit driving in the ON position and the OFF position.

According to the third advantageous configuration example, the first application-part plug contact is preferably connected to the first motor winding in an electrically conducting manner, the second application-part plug contact is connected to the second motor winding in an electrically conducting manner, and the third application-part plug contact is connected to the third motor winding in an electrically conducting manner.

Preferably, first to third application-part plug contacts are provided which are adapted to engage corresponding first to third supply-cable plug contacts.

Preferably, two supply-cable plug contacts each have two independent, different contact zones.

Advantageously, the first supply-cable plug contact and/or the second supply-cable plug contact are connected/connectable via a contact bridge to the readout antenna located in the electrical supply cable.

Preferably, the contact bridge opens when the application-part plug contact is moved from the OFF position to the ON position, so that in other words the contact bridge to the readout antenna is interrupted.

Preferably, at least one application-part plug contact is insulating at its tip.

It is advantageous if the contact bridge/switching bridge is adapted to be reset in a self-resilient manner or via a spring-loaded element.

In a fourth advantageous configuration example, an accessory, in particular a tool attachment, attachment, support foot or tool, is provided, which is attachable or attached to the surgical application part, wherein the accessory has a further, second RFID chip, which can be excited and read out via a second readout antenna provided in the surgical application part.

Preferably, the first readout antenna and the second readout antenna are arranged in series in a switching circuit and are connected to the control unit via the electrical supply cable.

Alternatively, the first readout antenna and the second readout antenna can be arranged in parallel in their own switching circuit and can be connected to the control unit via the electrical supply cable.

BRIEF DESCRIPTION OF THE DRAWING FIGURES

The invention is further explained hereinafter with the aid of figures. The following is shown:

DETAILED DESCRIPTION

Hereinafter, configuration examples of the present disclosure are described based on the accompanying figures.

The figures are merely schematic in nature and are provided solely for the purpose of understanding the invention. Identical elements are indicated by the same reference signs. The features of the individual configuration examples/forms can be interchanged.

Figure 1:
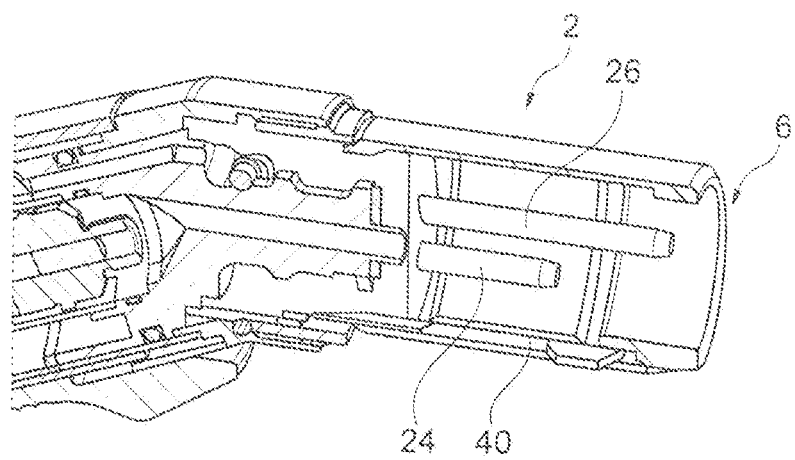
FIG. 1 shows a first sectional view of a surgical application part according to a first preferred configuration example.
Figure 2:
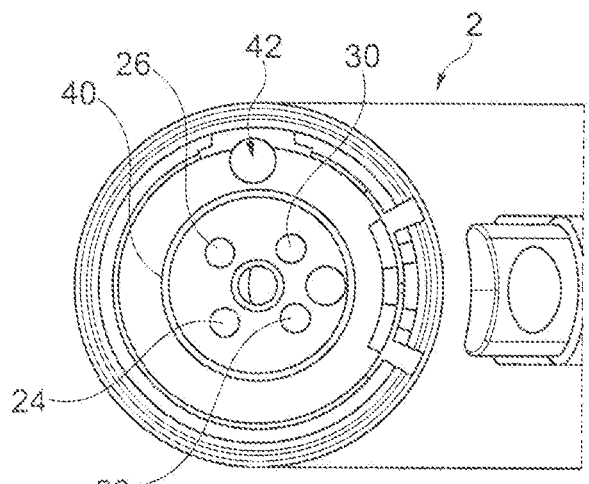
FIG. 2 shows a second sectional view of the surgical application part according to the first preferred configuration example.
Figure 3:
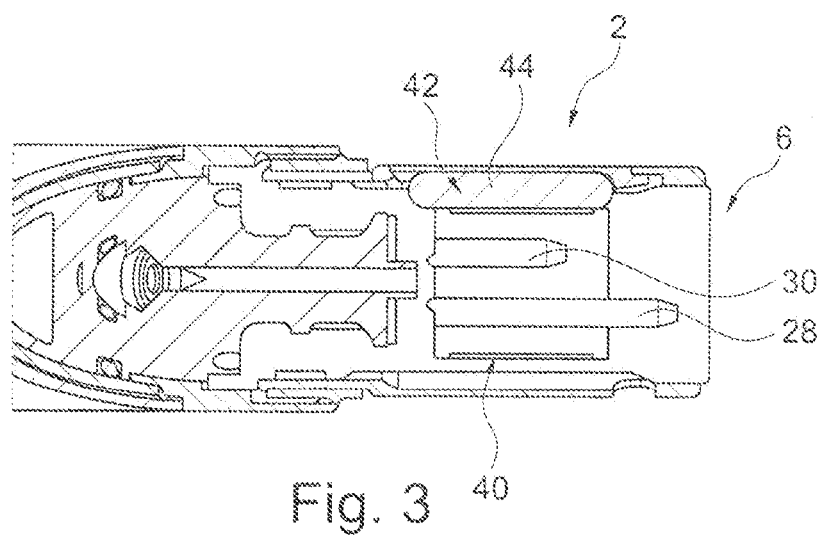
FIG. 3 shows a third sectional view of the surgical application part according to the first preferred configuration example.
Figures 4, 5, 6:
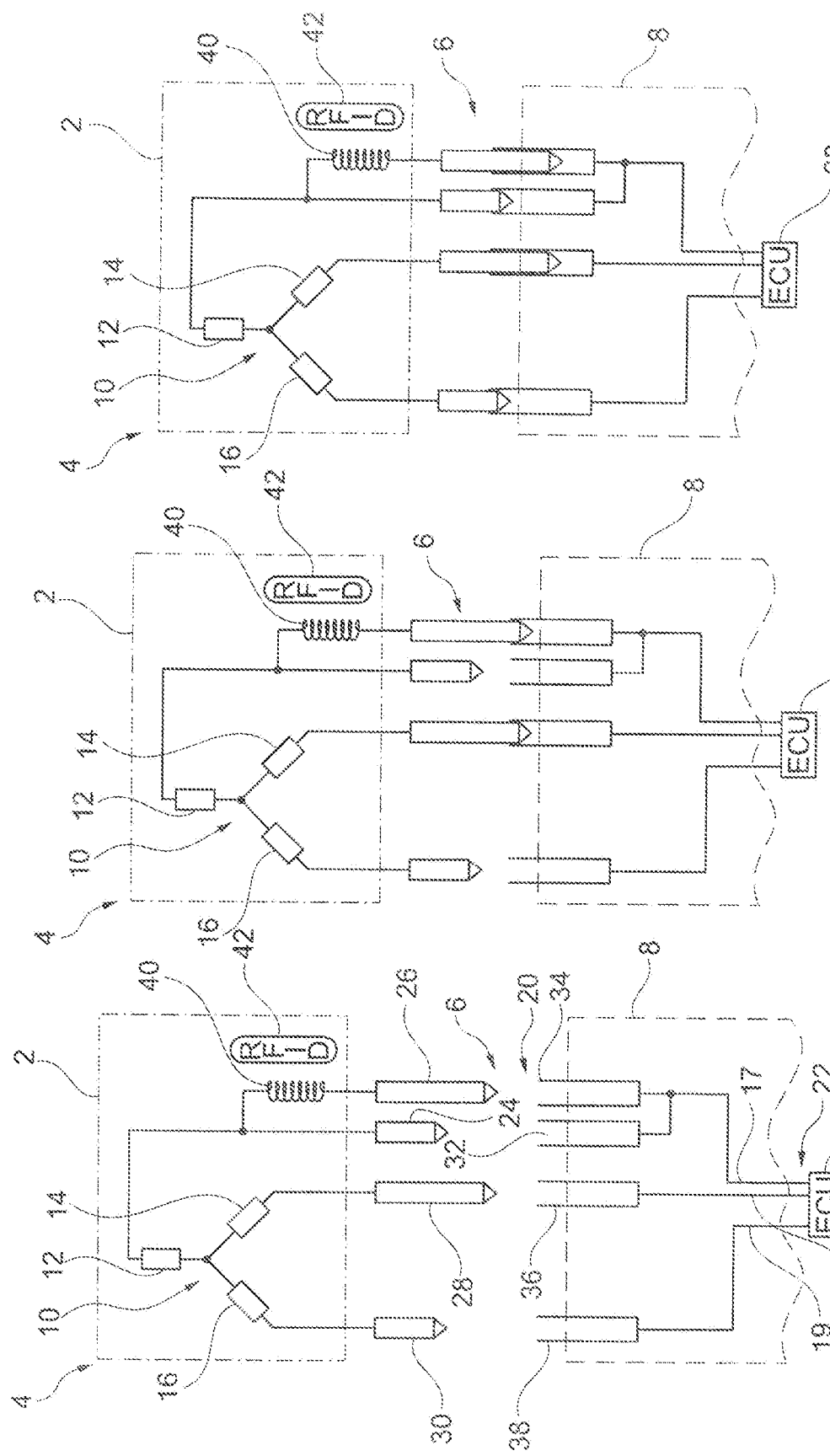
FIG. 4 shows a circuit diagram of a surgical device according to the first preferred configuration example, in which the surgical application part and an electrical supply cable are not (yet) mechanically coupled to each other.
FIG. 5 shows a circuit diagram of the surgical device according to the first preferred configuration example, in which the surgical application part and the electrical supply cable are mechanically coupled to each other and are in an electrical OFF position.
FIG. 6 shows a circuit diagram of the surgical device according to the first preferred configuration example, in which the surgical application part and the electrical supply cable are mechanically coupled to each other and are in an electrical ON position.

FIG. 1, FIG. 2 and FIG. 3 show sectional views of a surgical application part/handpiece 2 of a surgical device 4 according to a first preferred configuration example. FIG. 4, FIG. 5 and FIG. 6 show circuit diagrams in a coupling region 6 between the surgical device 4 and an electrical supply cable 8.

As shown in particular in FIG. 4, FIG. 5 and FIG. 6, the surgical application part 2 comprises an electric motor 10. The electric motor 10 comprises three motor windings, namely a first motor winding 12, a second motor winding 14 and a third motor winding 16. The three motor windings 12, 14, 16 are interconnected in a star configuration.

The electrical supply cable 8 has three lines/litz wires 17, 18, 19. The three lines 17, 18, 19 supply power to the three motor windings 12, 14, 16. At a first end 20, the electrical supply cable 8 is connected/connectable to the surgical application part 2 in the coupling region 6. At a second end 22, the electrical supply cable 8 is connected/connectable to a control unit 23. The control unit 23 is basically adapted to control the electric motor 10.

The surgical application part 2 has four application-part plug contacts, namely a first application-part plug contact 24, a second application-part plug contact 26, a third application-part plug contact 28, and a fourth application-part plug contact 30. The application-part plug contacts 24, 26, 28 and 30 are each formed pin-like/pin-shaped. The first application-part plug contact 24 and the fourth application-part plug contact 30 are of equal length. The second application-part plug contact 26 and the third application-part plug contact 28 are of equal length. The application-part plug contacts 24 and 30 are shorter than the application-part plug contacts 26 and 28.

The electrical supply cable 8 has four supply-cable plug contacts, namely a first supply-cable plug contact 32, a second supply-cable plug contact 34, a third supply-cable plug contact 36, and a fourth supply-cable plug contact 38. The supply-cable plug contacts 32, 34, 36 and 38 are each socket-like/socket-shaped.

The first to fourth application-part plug contacts 24, 26, 28, 30 are adapted to engage corresponding first to fourth supply-cable plug contacts 32, 34, 36 and 38 so that the surgical application part 2 is mechanically couplable to the electrical supply cable 8.

A readout antenna 40 is provided/integrated in the surgical application part 2. In addition, an RFID chip 42 is installed in the surgical application part 2. The RFID chip 42 has a glass shell 44. The readout antenna 40 is—as can be seen in particular from FIG. 2, FIG. 3, but also from the circuit diagrams in FIG. 4, FIG. 5 or FIG. 6—arranged in close proximity to the RFID chip 42. In particular, the distance between the readout antenna 40 and the RFID chip 42 is less than or equal to 1 cm, preferably less than or equal to 5 mm, particularly preferably less than or equal to 2 mm. The readout antenna 40 is basically capable of being supplied with voltage and is adapted to excite and read out the RFID chip 42 in order to transmit data bidirectionally between the RFID chip 42 and the control unit 23 via the electrical supply cable 8.

The first motor winding 12 is connected to the first application-part plug contact 24 in an electrically conducting manner. In addition, the first motor winding 12 is connected to the readout antenna 40 in an electrically conducting manner. The readout antenna 40 is in turn connected to the second application-part plug contact 26 in an electrically conducting manner. The second motor winding 14 is connected to the third application-part plug contact 28 in an electrically conducting manner. The third motor winding 16 is connected to the fourth application-part plug contact 30 in an electrically conducting manner.

The first supply-cable plug contact 32 and the second supply-cable plug contact 34 are connected to a first line 17 in an electrically conducting manner. The third supply-cable plug contact 36 is connected to a second line 18 in an electrically conducting manner. The fourth supply-cable plug contact 38 is connected to a third line 19 in an electrically conducting manner.

In the circuit diagram shown in FIG. 4, the surgical application part 2 and the electrical supply cable 8 are not yet mechanically coupled to each other. In the circuit diagrams shown in FIG. and FIG. 6, the surgical application part 2 and the electrical supply cable 8 are mechanically coupled. Basically, when the surgical application part 2 and the electrical supply cable 8 are coupled to each other, two electrical switching positions are adjustable, namely an OFF position, which is illustrated in FIG. 5, and an ON position, which is illustrated in FIG. 6.

In the OFF position, the second application-part plug contact 26 is connected to the second supply-cable plug contact 34 in an electrically conducting manner. The first application-part plug contact 24 is not connected to the first supply-cable plug contact 32 in an electrically conducting manner. The third application-part plug contact 28 is connected to the third supply-cable plug contact 36 in an electrically conducting manner. The fourth application-part plug contact 30 is not connected to the fourth supply-cable plug contact 38 in an electrically conducting manner.

In the OFF position, the readout antenna 40 is supplied with voltage or, respectively, a voltage is applied to the readout antenna 40. The RFID chip 42 can therefore be excited and read out in the OFF position and bidirectional data and energy transmission between the control unit 23 and the RFID chip 42 is enabled.

In the ON position (see FIG. 6) all four application-part plug contacts 24, 26, 28, 30 are connected to the four supply-cable plug contacts 32, 34, 36, 38 in an electrically conducting manner. The branch/switching circuit containing the readout antenna 40 is short-circuited when the first application-part plug contact 24 is connected to the first supply-cable plug contact 32 in an electrically conducting manner, so that no voltage is applied to the readout antenna 40. In the ON position, the readout antenna 40 is consequently taken out of operation and motor operation of the surgical device 4 can take place.

Figure 7:
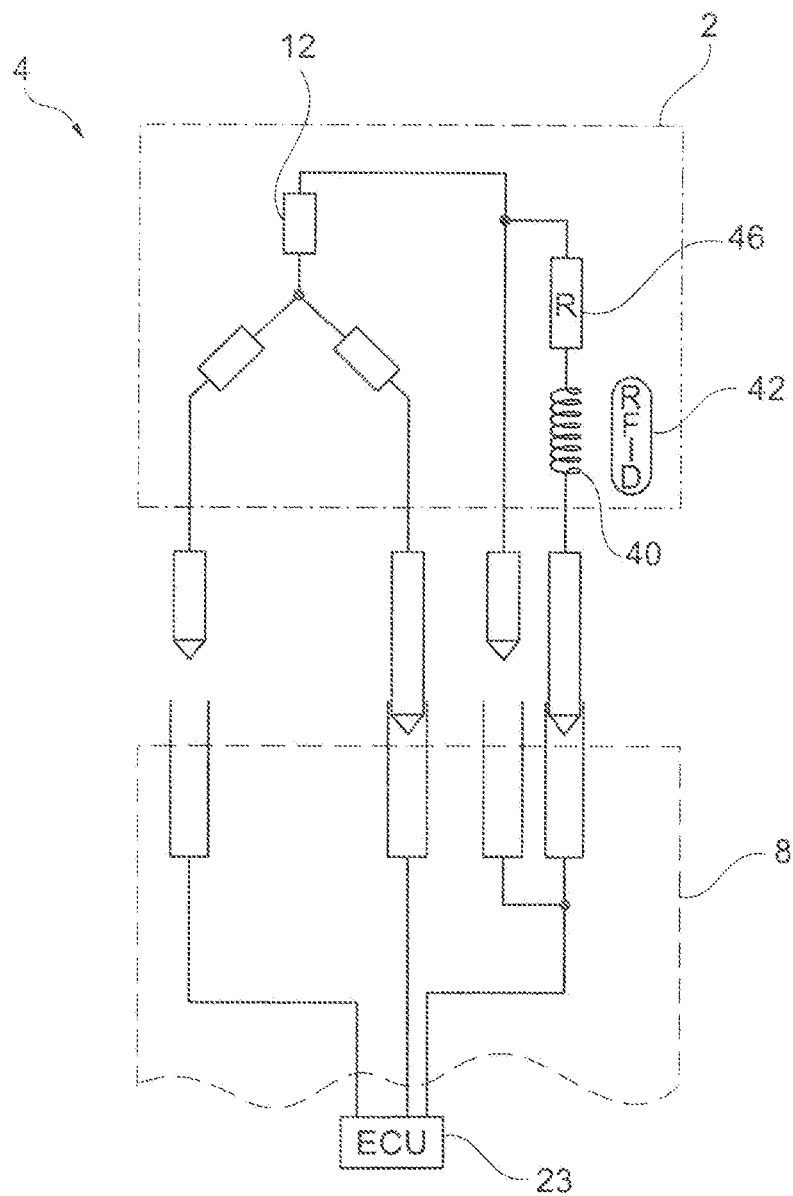
FIG. 7 shows a circuit diagram of the surgical device according to a variation of the first preferred configuration example, in which a detection resistor is provided in addition to a readout antenna.

As shown in FIG. 7, in the first configuration example of the invention, an encoding/detection resistor 46 may additionally be provided, which is connected in series with the readout antenna 40. Using the detection resistor 46, in the OFF position, which is shown in FIG. 7, the surgical application part 2, in particular the electric motor 10 of the surgical application part 2, can be detected. In the ON position, the switching circuit/branch for the detection resistor 46 is short-circuited and taken out of operation. In FIG. 7, the first motor winding 12 is connected to the detection resistor 46 in an electrically conducting manner, the detection resistor 46 is connected to the readout antenna 40 in an electrically conducting manner, and the readout antenna 40 is connected to the second application-part plug contact 26 in an electrically conducting manner. However, it would also be possible for the first motor winding 12 to be connected to the readout antenna 40, the readout antenna 40 to be connected to the detection resistor 46, and the detection resistor 46 to be connected to the second application-part plug contact 26.

Figure 8:
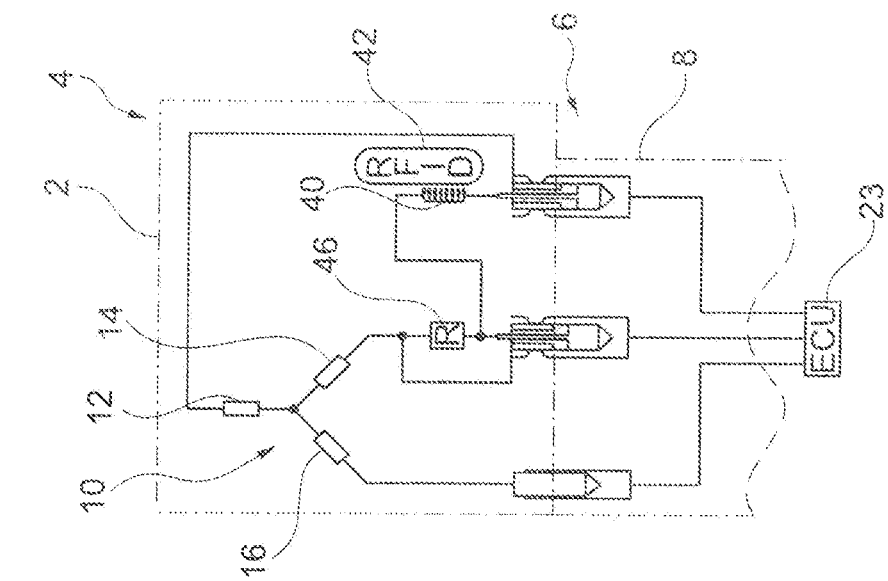
FIG. 8 shows a circuit diagram of a surgical device according to a second preferred configuration example, in which a surgical application part and an electrical supply cable are not (yet) mechanically coupled to each other.
Figure 9:
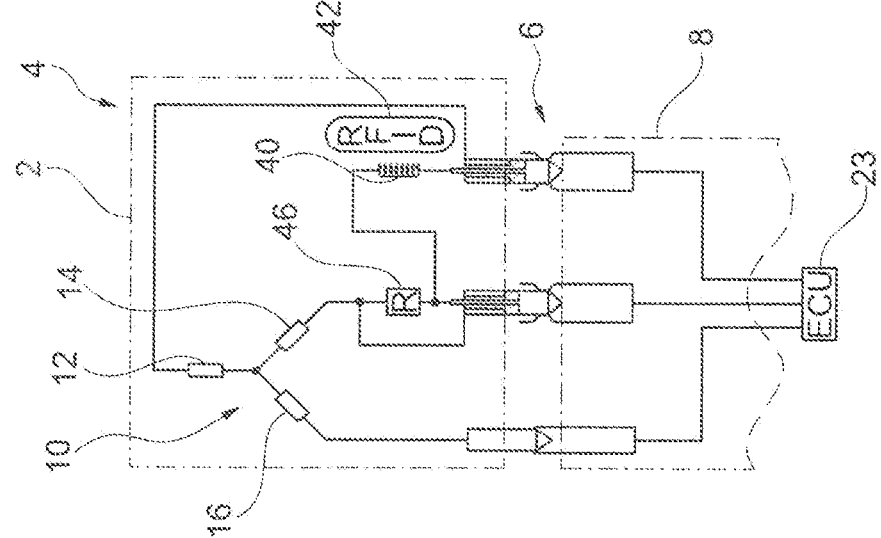
FIG. 9 shows a circuit diagram of the surgical device according to the second preferred configuration example, in which the surgical application part and the electrical supply cable are mechanically coupled to each other and are in an electrical OFF position.
Figure 10:
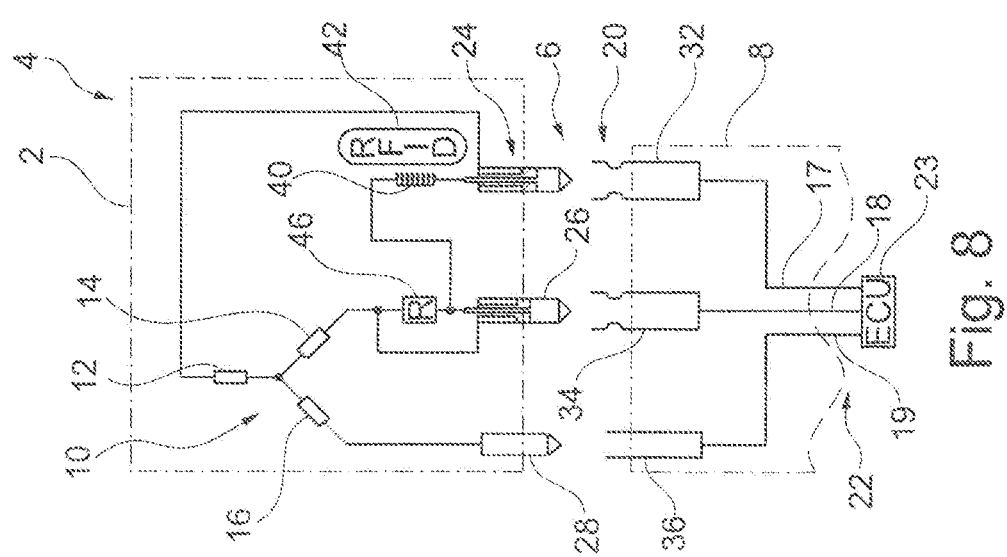
FIG. 10 shows a circuit diagram of the surgical device according to the second preferred configuration example, in which the surgical application part and the electrical supply cable are mechanically coupled to each other and are in an electrical ON position.

FIG. 8, FIG. 9 and FIG. 10 show circuit diagrams of a second preferred configuration example of the invention. Again, the surgical application part 2 includes an electric motor 10 having three motor windings 12, 14, 16 interconnected in a star configuration. The electrical supply cable 8 has three lines 17, 18, 19 which supply power to the three motor windings 12, 14, 16. At a first end 20, the electrical supply cable 8 is connected/connectable to the surgical application part 2 in a coupling region 6. At a second end 22, the electrical supply cable 8 is connected/connectable to a control unit 23. The control unit 23 is basically arranged to control the electric motor 10.

The surgical application part 2 has three application-part plug contacts, namely a first application-part plug contact 24, a second application-part plug contact 26, and a third application-part plug contact 28. The application-part plug contacts 24, 26 and 28 are each pin-like/pin-shaped and are preferably of equal length. The electrical supply cable 8 has three supply-cable plug contacts, namely a first supply-cable plug contact 32, a second supply-cable plug contact 34, and a third supply-cable plug contact 36. The supply-cable plug contacts 32, 34 and 36 are each socket-like/socket-shaped.

The first to third application-part plug contacts 24, 26 and 28 are adapted to engage corresponding first to third supply-cable plug contacts 32, 34 and 36 so that the surgical application part 2 is mechanically couplable to the electrical supply cable 8.

The first supply-cable plug contact 32 is connected to a first line 17 in an electrically conducting manner. The second supply-cable plug contact 34 is connected to a second line 18 in an electrically conducting manner. The third supply-cable plug contact 36 is connected to a third line 19 in an electrically conducting manner.

A readout antenna 40 is provided/integrated in the surgical application part 2. In addition, an RFID chip 42 is installed in the surgical application part 2, which has a glass shell 44. The readout antenna 40 is arranged in close proximity to the RFID chip 42. That means the distance between the readout antenna 40 and the RFID chip 42 is equal to or less than 1 cm, preferably equal to or less than 5 mm, particularly preferably equal to or less than 2 mm. The readout antenna 40 is basically capable of being supplied with voltage and is adapted to excite and read out the RFID chip 42 in order to transmit data bidirectionally between the RFID chip 42 and the control unit 23 via the electrical supply cable 8. In addition, a detection resistor 46 is preferably provided in the surgical application part 2.

Figure 11:
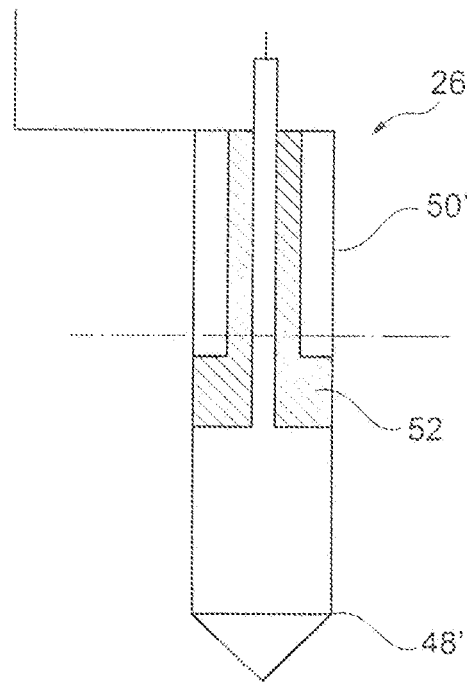
FIG. 11 shows a configuration of a second application-part plug contact of the surgical application part according to the second preferred configuration example.
Figure 12:
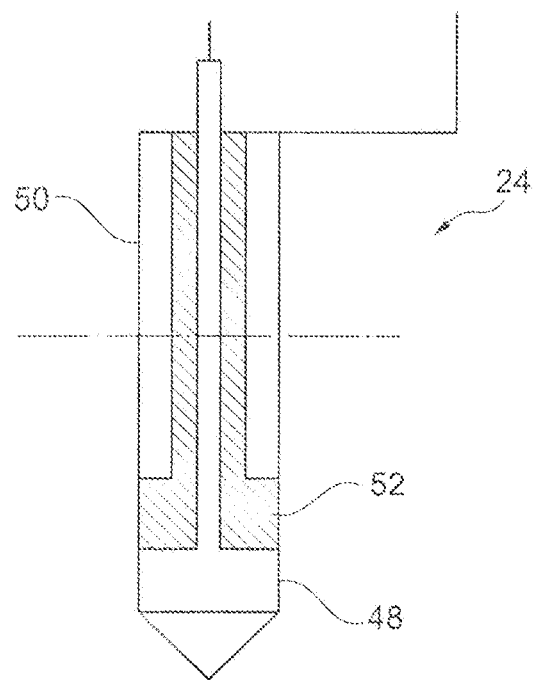
FIG. 12 shows a configuration of a first application-part plug contact of the surgical application part according to the second preferred configuration example.

The first application-part plug contact 24 and the second application-part plug contact 26 each have two independent, different contact zones. In particular, the first application-part plug contact 24 has a first contact zone 48 and a second contact zone 50 (see FIG. 12). The second application-part plug contact 26 also has a first contact zone 48' and a second contact zone 50' (see FIG. 11). The two contact zones 48/48' and 50/50' are spaced apart in the axial direction of the application-part plug contacts 24, 26.

The first contact zone 48 of the first application-part plug contact 24 is connected to the readout antenna 40 in an electrically conducting manner. The second contact zone 50 of the first application-part plug contact is connected to the first motor winding 12 in an electrically conducting manner. The first contact zone 48' of the second application-part plug contact 26 is connected to the readout antenna 40 and the detection resistor 46 in an electrically conducting manner. The second contact zone 50' of the second application-part plug contact 26 is connected to the second motor winding 14 in an electrically conducting manner. The third application-part plug contact 28 is connected to the third motor winding 16 in an electrically conducting manner. The first and second contact zones 48, 48' and 50, 50' are separated from each other by an insulator 52.

In the circuit diagram shown in FIG. 8, the surgical application part 2 and the electrical supply cable 8 are not yet mechanically coupled to each other. In the circuit diagrams shown in FIG. 9 and FIG. 10, the surgical application part 2 and the electrical supply cable 8 are mechanically coupled. Basically, when the surgical application part 2 and the electrical supply cable 8 are coupled to each other, two electrical switching positions are adjustable, namely an OFF position, which is illustrated in FIG. 9, and an ON position, which is illustrated in FIG. 10.

Since the first application-part plug contact 24 and the second application-part plug contact 26 each have two contact zones, a different switching circuit control can be realized in the ON position and the OFF position.

In the OFF position, the first contact zone 48 of the first application-part plug contact 24 is connected to the first supply-cable plug contact 32 in an electrically conducting manner. The first contact zone 48' of the second application-part plug contact 26 is connected to the second supply-cable plug contact 34 in an electrically conducting manner. The third application-part plug contact 28 is connected to the third supply-cable plug contact 36 in an electrically conducting manner.

In the OFF position, the detection resistor 46 is read out across the motor windings 14, 16 via contact points between the third application-part plug contact 28 and the third supply-cable plug contact 36 on the one hand, and between the second application-part plug contact 26 and the second supply-cable plug contact 34 on the other hand. At the same time, the readout antenna 40 is addressed via contact points between the second application-part plug contact 26 and the second supply-cable plug contact 34 on the one hand, and between the first application-part plug contact 24 and the first supply-cable plug contact 32 on the other hand. The sockets of the supply-cable plug contacts 32 and 34 each contact only a front part of the application-part plug contacts 24, 26, i.e. respectively the first contact zones 48, 48' of the application-part plug contacts 24, 26.

The first and second contact zones 48, 48', 50, 50' of the two application-part plug contacts 24, 26 are designed in such a way that when changing from the OFF position to the ON position, the contact zones do not change simultaneously but one after the other. Accordingly—as can be seen from FIG. 11 and FIG. 12—the first contact zone 48 of the first application-part plug contact 24 is shorter in the axial direction than the first contact zone 48' of the second application-part plug contact 26. Accordingly, the second contact zone 50 of the first application-part plug contact 24 is longer in the axial direction than the second contact zone 50' of the second application-part plug contact 26.

If the contact zones do not change simultaneously but one after the other, it is ensured that the contact between the surgical application part 2 and the control unit 23 is never interrupted when switching from the OFF position to the ON position. In this way, the functionality of the electronics can be guaranteed.

In the ON position, the second contact zone 50 of the first application-part plug contact 24 is connected to the first supply-cable plug contact 32 in an electrically conducting manner. The second contact zone 50' of the second application-part plug contact 26 is connected to the second supply-cable plug contact 34 in an electrically conducting manner. The detection resistor 46 and the readout antenna 40 are short-circuited and taken out of operation so that motor operation can take place.

Figures 13, 14, 15:
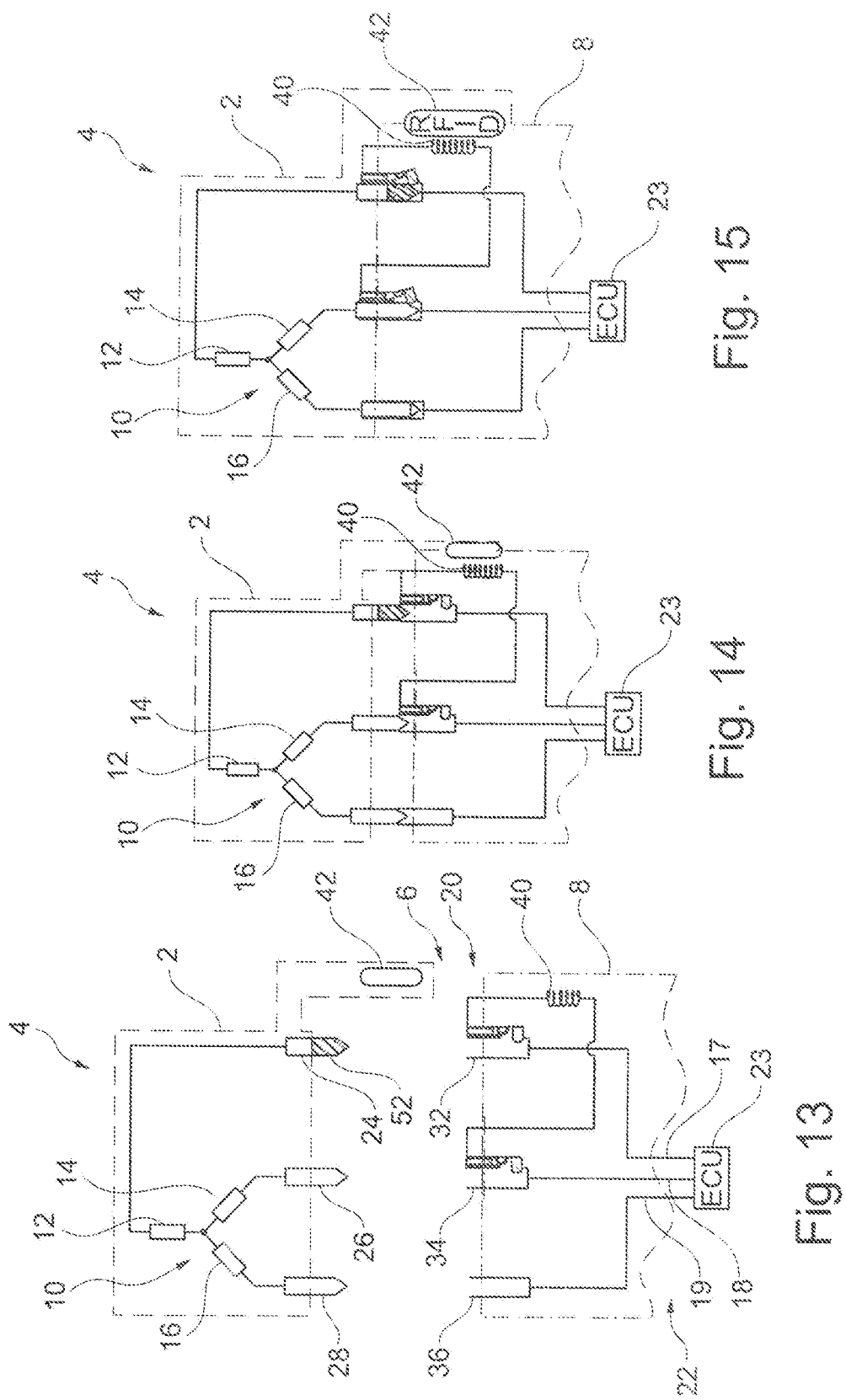
FIG. 13 shows a circuit diagram of a surgical device according to a third preferred configuration example, in which a surgical application part and an electrical supply cable are not (yet) mechanically coupled to each other.
FIG. 14 shows a circuit diagram of the surgical device according to the third preferred configuration example, in which the surgical application part and the electrical supply cable are mechanically coupled to each other and are in an electrical OFF position.
FIG. 15 shows a circuit diagram of the surgical device according to the third preferred configuration example, in which the surgical application part and the electrical supply cable are mechanically coupled to each other and are in an electrical ON position.

FIG. 13, FIG. 14 and FIG. 15 show circuit diagrams of a third preferred configuration example of the invention. Again, the surgical application part 2 includes an electric motor 10 having three motor windings 12, 14, 16 interconnected in a star configuration. The electrical supply cable 8 has three lines 17, 18, 19 which supply power to the three motor windings 12, 14, 16. At a first end 20, the electrical supply cable 8 is connected/connectable to the surgical application part 2 in a coupling region 6. At a second end 22, the electrical supply cable 8 is connected/connectable to a control unit 23. The control unit 23 is basically adapted to control the electric motor 10.

The surgical application part 2 has three application-part plug contacts, namely a first application-part plug contact 24, a second application-part plug contact 26, and a third application-part plug contact 28. The application-part plug contacts 24, 26 and 28 are each pin-like/pin-shaped and are of equal length. The first application-part plug contact 24 is insulating at its tip/has an insulator 52. The electrical supply cable 8 has three supply-cable plug contacts, namely a first supply-cable plug contact 32, a second supply-cable plug contact 34, and a third supply-cable plug contact 36. The supply-cable plug contacts 32, 34 and 36 are each socket-like/socket-shaped.

The first to third application-part plug contacts 24, 26 and 28 are adapted to engage corresponding first to third supply-cable plug contacts 32, 34 and 36 so that the surgical application part 2 is mechanically couplable to the electrical supply cable 8.

The first application-part plug contact 24 is connected to the first motor winding 12 in an electrically conducting manner. The second application-part plug contact 26 is connected to the second motor winding 14 in an electrically conducting manner. The third application-part plug contact is connected to the third motor winding 16 in an electrically conducting manner.

An RFID chip 42 is installed in the surgical application part 2, which has a glass shell 44.

According to the third preferred configuration example, the readout antenna 40 is not provided in the surgical application part 2 but in the electrical supply cable 8.

Two supply-cable plug contacts, namely in this case the first supply-cable plug contact 32 and the second supply-cable plug contact 34, each have two independent, different contact zones for different switching-circuit driving in the ON position and in the OFF position. In principle, it would also be sufficient (for the circuit principle) if only one supply-cable plug contact, for example only the first supply-cable plug contact 32 or only the second supply-cable plug contact 34, has two contact zones. However, for redundant protection of the readout antenna 40 against malfunction in the event of a shutdown, it is recommended to provide two supply-cable plug contacts, each of which has two independent, different contact zones.

Figure 16:
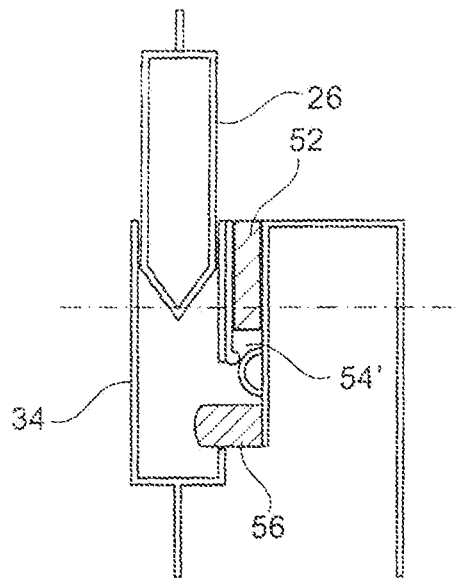
FIG. 16 shows a second application-part plug contact of the surgical application part and a second supply-cable plug contact of the electrical supply cable according to the third preferred configuration example, which are in the electrical OFF position.
Figure 17:
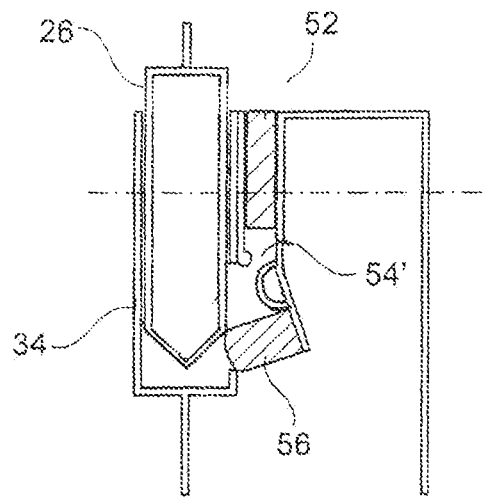
FIG. 17 shows the second application-part plug contact and the second supply-cable plug contact according to the third preferred configuration example, which are in the electrical ON position.
Figure 18:
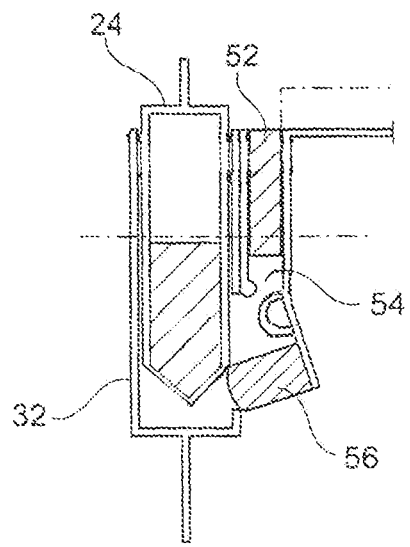
FIG. 18 shows the first application-part plug contact of the surgical application part and the first supply-cable plug contact of the electrical supply cable according to the third preferred configuration example, which are in the electrical ON position.
Figure 19:
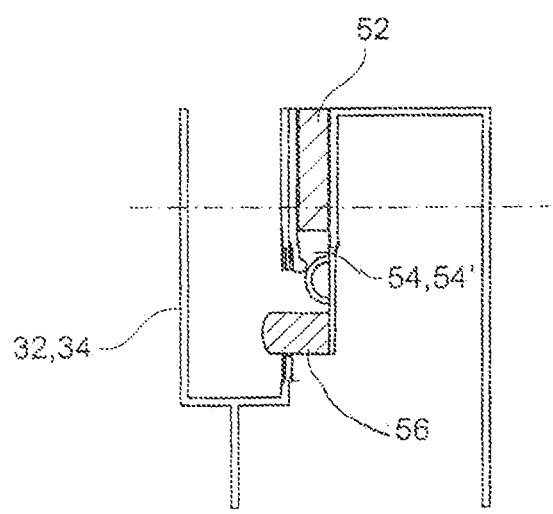
FIG. 19 shows a supply-cable plug contact with two contact zones according to the third preferred configuration example in the ON position.

In the OFF position, the first supply-cable plug contact 32 and the second supply-cable plug contact 34 are connected to the readout antenna 40 in an electrically conducting manner via a contact bridge 54, 54' (see FIG. 14 and FIG. 16). When changing from the OFF position to the ON position (see FIG. 15, FIG. 17, FIG. 18, FIG. 19), the contact bridges 54, 54' to the readout antenna 40 are simultaneously interrupted by the application-part plug contacts 24, 26. When the application-part plug contacts 24, 26 are further inserted into the supply-cable plug contacts 32, 34 during the change from the OFF position to the ON position, they encounter an insulating projection 56 which can be deflected by the application-part plug contacts 24, 26, causing the contact bridges 54, 54' to open. Since the first application-part plug contact 24 is insulating at its tip/has an insulator 52, the interruption can also be maintained without problems. An insulator 52 is provided between the supply-cable plug contacts 32, 34 and the switching circuit of the readout antenna 40 in order to prevent unintentional contacting between a supply-cable plug contact 32, 34 and the switching circuit of the readout antenna 40 when the contact bridge 54, 54' is open. When the application-part plug contacts 24, 26 are led out of the supply-cable plug contacts 32, 34 again, the insulating projection 56 is reset self-resiliently or by a spring-loaded element and the contact bridges 54, 54' are closed again.

In summary, the readout antenna 40 in the electrical supply cable 8 can be addressed in the OFF position via contact points between the first application-part plug contact 24 and the first supply-cable plug contact 32 on the one hand, and between the second application-part plug contact 26 and the second supply-cable plug contact 34 on the other hand. If the electrical supply cable 8 and the surgical application part 2 are mechanically coupled to each other (see FIG. 14 or FIG. 15), the readout antenna 40 is arranged in close proximity to the RFID chip 42. The readout antenna 40 is capable of being supplied with voltage and is adapted to excite and read out the RFID chip 42 in order to transmit data bidirectionally between the RFID chip 42 and the control unit 23 via the electrical supply cable 8. In the ON position, the contact bridges 54, 54' are open/interrupted and motor operation can take place.

Figure 20:
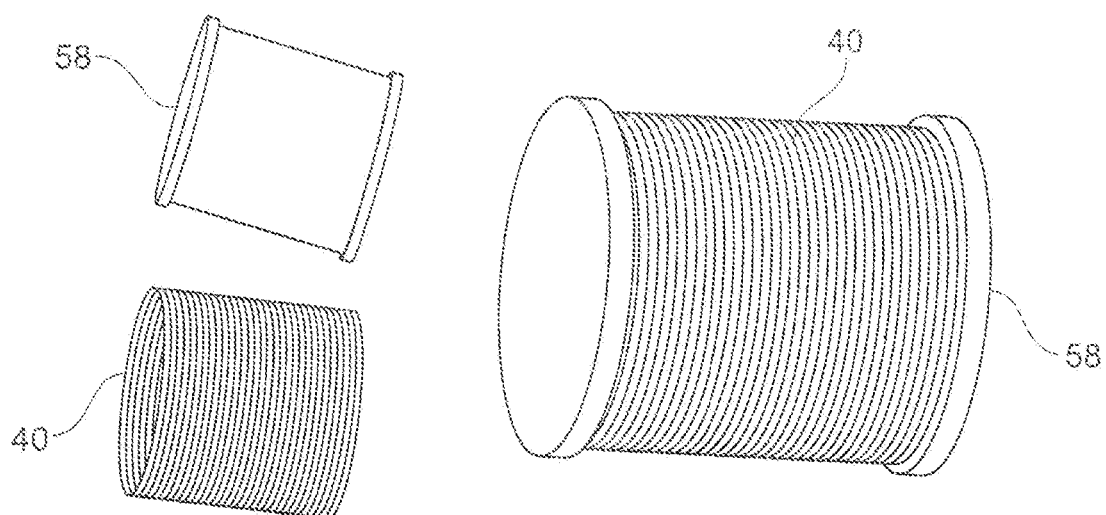
FIG. 20 shows an embodiment of a sleeve-like antenna carrier with a coil-shaped readout antenna.
Figure 21:
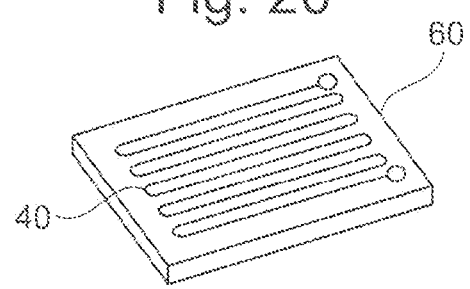
FIG. 21 shows an embodiment of a flat circuit board/insertion plate with a meander-shaped readout antenna.
Figure 22:
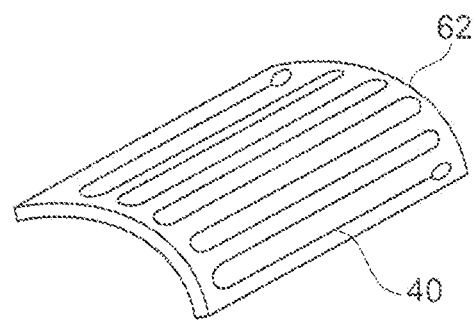
FIG. 22 shows an embodiment of a flexible circuit board/insertion plate with a meander-shaped readout antenna.
Figure 23:
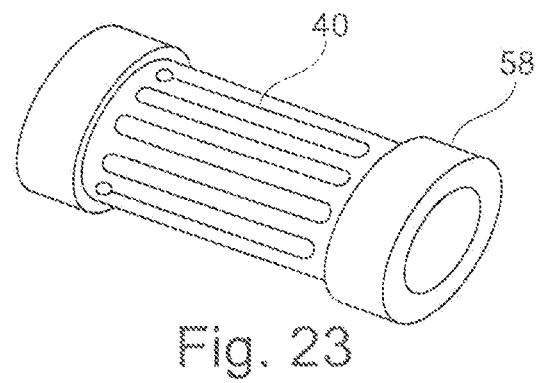
FIG. 23 shows an embodiment of a antenna carrier made of plastic with a printed/vapor-deposited, meander-shaped readout antenna.

FIGS. 20 to 23 show embodiments/options of how the readout antenna 40 could be integrated into the surgical application part 2 or the electrical supply cable 8. FIG. 20 shows the embodiment which is also realized in FIG. 2 or FIG. 3. In FIG. 20, a sleeve-like antenna carrier 58 is provided, which carries the readout antenna 40 which is in the form of a coil/coil-shaped. In FIG. 21, a flat circuit board/insertion plate 60 is provided, on which a meander-shaped readout antenna 40 is applied. In FIG. 22, a flexible circuit board/insertion plate 62 is provided, on which a meander-shaped readout antenna 40 is applied. In FIG. 23, an antenna carrier 58 (insertion part/functional part) made of plastic is provided, on which a meander-shaped readout antenna 40 is printed or vapor-deposited. The antenna carrier 58 is a sleeve made of plastic and forms an insulating contact carrier. It is entirely possible, and is also provided, for readout antennas 40 to be integrated in this way subsequently in series products already in circulation.

Figure 24:
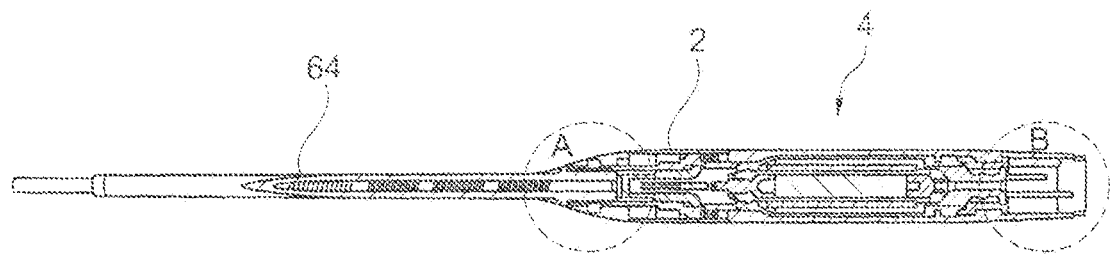
FIG. 24 shows a sectional view of a surgical device with tool attachment according to a (fourth) configuration example.
Figure 25:
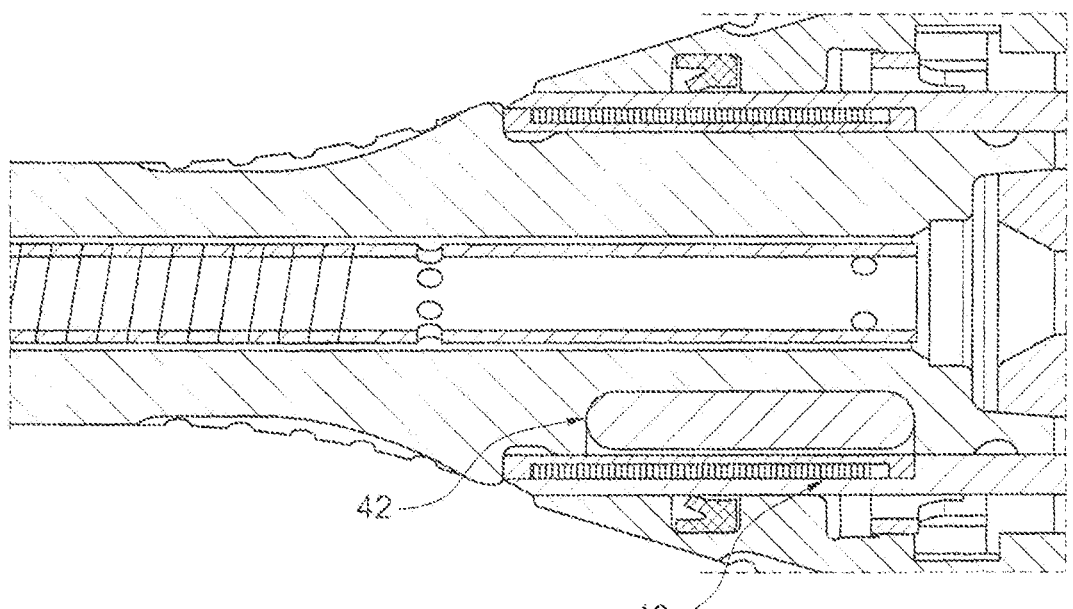
FIG. 25 shows a sectional view of a detail A of the surgical device shown in FIG. 24.
Figure 26:
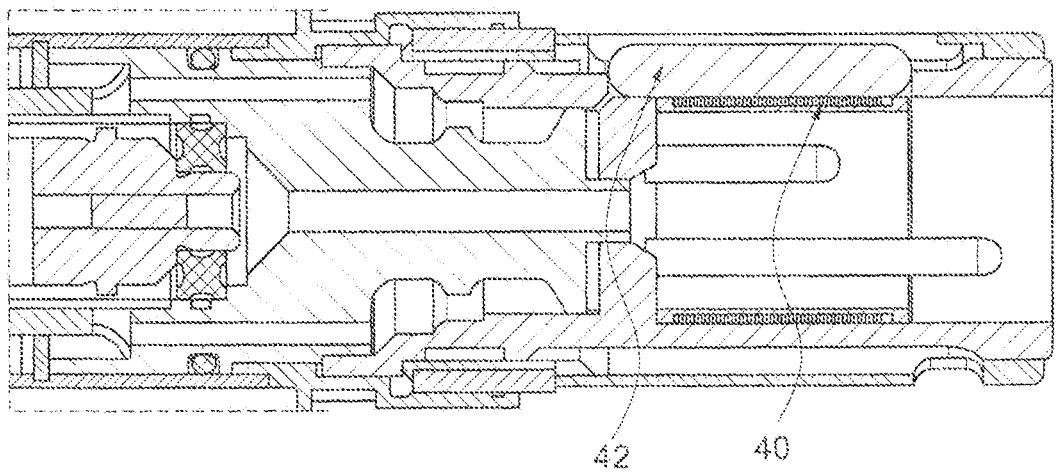
FIG. 26 shows a sectional view of a detail B of the surgical device shown in FIG. 24.

FIG. 24 shows a configuration example in which the surgical device 4 has a tool attachment (accessory) 64 attached to the surgical application part 2. FIG. 25 shows detail A shown in FIG. 24, and FIG. 26 shows detail B shown in FIG. 24. From FIG. 25, it can be seen that the tool attachment 64 has an RFID chip 42. This can be excited and read out via a readout antenna 40 provided in the surgical application part 2, which is arranged in close proximity to the RFID chip 42. As can be seen from FIG. 26, the surgical application part 2 also has an RFID chip 42 which can be excited and read out by the further readout antenna 40. According to this configuration example, two readout antennas 40 and one RFID chip 42 are provided in the surgical application part. An RFID chip 42 is provided in the tool attachment.

The first readout antenna 40 and the second readout antenna 40 can be arranged in series in a switching circuit and can be connected to the control unit 23 via the electrical supply cable 8. Alternatively, the first readout antenna 40 and the second readout antenna 40 can be arranged in parallel in their own switching circuit and can be connected to the control unit 23 via the electrical supply cable 8.

The invention claimed is:

1. A surgical device comprising:
a surgical application part with an electric motor having motor windings;
an electrical supply cable having a plurality of lines; and
at least one readout antenna which is integrated in the surgical application part or the electrical supply cable,
the electrical supply cable being connectable at a first end to the surgical application part and at a second end to a control unit for controlling the electric motor,
the at least one readout antenna being capable of being supplied with voltage and being designed as an additional element separate from the motor windings,
the at least one readout antenna adapted to excite and read out an RFID chip arranged or arrangeable near the at least one readout antenna to transmit data bidirectionally between the RFID chip and the control unit via the electrical supply cable.

2. The surgical device according to claim 1, wherein the at least one readout antenna and the RFID chip are arranged or arrangeable at a distance from each other of less than or equal to 1 cm.

3. The surgical device according to claim 1, wherein the at least one readout antenna is meander-shaped or spiral-shaped or coil-shaped or helix-shaped.

4. The surgical device according to claim 1, wherein the plurality of lines comprises three lines.

5. The surgical device according to claim 4, wherein the motor windings comprise three motor windings configured to be supplied with current and driven via the three lines.

6. The surgical device according to claim 1, wherein the RFID chip is integrated in the surgical application part.

7. The surgical device according to claim 1, wherein the surgical application part has a plurality of application-part plug contacts and the electrical supply cable has a plurality of supply-cable plug contacts, wherein the application-part plug contacts and the supply-cable plug contacts are engageable with each other in order to couple the surgical application part to the electrical supply cable.

8. The surgical device according to claim 7, wherein when the surgical application part and the electrical supply cable are coupled to each other, at least two electrical switching positions are adjustable, the at least two electrical switching positions comprising an OFF position and an ON position, wherein in the OFF position the at least one readout antenna gets or is supplied with voltage and the RFID chip can thus be excited and read out, and wherein in the ON position the at least one readout antenna is not supplied with voltage.

9. The surgical device according to claim 8, wherein the application-part plug contacts are pin-shaped and at least one application-part plug contact has two independent, different contact zones for different switching-circuit driving in the ON position and the OFF position.

10. The surgical device according to claim 8, wherein the supply-cable plug contacts are socket-shaped and at least one supply-cable plug contact has two independent, different contact zones for different switching-circuit driving in the ON position and the OFF position.

11. The surgical device according to claim 1, wherein the at least one readout antenna comprises a first readout antenna and a second readout antenna, wherein the second readout antenna is provided in the surgical application part, wherein an accessory is attachable or is attached to the surgical application part, and wherein the accessory has a further, second RFID chip configured to be excited and read out via the second readout antenna.

12. The surgical device according to claim 8, wherein in the ON position a switching circuit or circuit containing the at least one readout antenna gets or is short-circuited and is thus taken out of operation.

\* \* \* \* \*